US011759415B2

(12) United States Patent
Zimbardi et al.

(10) Patent No.: US 11,759,415 B2
(45) Date of Patent: Sep. 19, 2023

(54) COSMETIC COMPOSITION, METHOD FOR THE PRODUCTION OF *ASTROCARYUM VULGARE* OIL AND/OR BUTTER, USE OF THE COSMETIC COMPOSITION AND METHOD FOR THE PRODUCTION AND/OR PROTECTION AGAINST DEGRADATION OF HYALURONIC ACID IN THE SKIN

(71) Applicant: Natura Cosméticos S.A., São Paulo (BR)

(72) Inventors: Daniela Zimbardi, São Paulo (BR); Cintia Rosa Ferrari, São Paulo (BR); Juliana Beltrame Reigada, São Paulo (BR); Leticia Figueroa Gomes, São Paulo (BR); Priscila Caffeu Ramos Daniel, São Paulo (BR); Pedro Paulo Soldati, São Paulo (BR); Karina Moretti Da Silva, São Paulo (BR); Helen Andrade Arcuri, São Paulo (BR); Carolina Iatesta Domenico, São Paulo (BR); Felipe Shigueru Takano, São Paulo (BR); Melissa Dibbern Ganzerla, São Paulo (BR); Ana Luisa Abrahão Dias, São Paulo (BR); Fernanda Malanconi Thomaz, São Paulo (BR)

(73) Assignee: Natura Cosméticos S.A., São Paulo (BR)

( * ) Notice: Subject to any disclaimer, the term of this patent is extended or adjusted under 35 U.S.C. 154(b) by 0 days.

(21) Appl. No.: 17/291,479

(22) PCT Filed: Jun. 17, 2019

(86) PCT No.: PCT/BR2019/050226
§ 371 (c)(1),
(2) Date: May 5, 2021

(87) PCT Pub. No.: WO2020/093119
PCT Pub. Date: May 14, 2020

(65) Prior Publication Data
US 2022/0000761 A1 Jan. 6, 2022

(30) Foreign Application Priority Data

Nov. 5, 2018 (BR) .................... BR102018072738-9

(51) Int. Cl.
*A61K 8/9794* (2017.01)
*A61K 8/31* (2006.01)
*A61K 8/35* (2006.01)
*A61K 8/36* (2006.01)
*A61Q 17/00* (2006.01)
*A61Q 19/00* (2006.01)

(52) U.S. Cl.
CPC .............. *A61K 8/9794* (2017.08); *A61K 8/31* (2013.01); *A61K 8/35* (2013.01); *A61K 8/361* (2013.01); *A61Q 17/00* (2013.01); *A61Q 19/007* (2013.01)

(58) Field of Classification Search
None
See application file for complete search history.

(56) References Cited

U.S. PATENT DOCUMENTS

2003/0138507 A1 7/2003 Pauly et al.
2003/0147976 A1 8/2003 Polezel
2012/0269914 A1 10/2012 Susilo

FOREIGN PATENT DOCUMENTS

FR 2957258 A1 9/2011
WO WO 2004/021971 A2 3/2004

OTHER PUBLICATIONS

Bonnafous et al. (FR2885296A1 machine translation) (Year: 2006).*
Bony et al. ("Awara (*Astrocaryum vulgare* M.) pulp oil: Chemical characterization, and anti-inflammatory properties in a mice model of endotoxic shock and a rat model of pulmonary inflammation", Fitoterapia 83 (2012) 33-43). (Year: 2012).*
International Searching Authority, International Search Report and Written Opinion received for International Application No. PCT/BR2019/050226, dated Sep. 12, 2019, 14, pages, National Institute of Industrial Property, Brazil.
Anonymous, "Body Anti-Aging Firming Cream", Jan. 11, 2018, retrieved from the Internet at <http://www.gndp.com>, Mintel Database accession No. 5329957, 6 pages.
Baldissera, Matheus D., "Antihyperglycemic, antioxidant activities of tucumã oil (Astrocaryum vulgare) in alloxan-induced diabetic mice, and identification of fatty acid profile by gas chromatograph: New natural source to treat hyperglycemia", Abstract and Introduction, May 25, 2017, Chemio-Biological Interactions, retrieved from the Internet at <https://www.sciencedirect.com/science/article/abs/pii/ S0009279717302466?via%3Dihub> on Apr. 17, 2023, 11 pages.
European Patent Office, Extended European Search Report received for Application No. 19881840.3, dated Sep. 15, 2022, 12 pages, Germany.
Jarchem Industries, Inc., "Jarchem's Global Portfolio: Jarchem Innovative Ingredients", Jan. 1, 2015, retrieved from the Internet at <http://www.jarchem.com/images/brochures/personal_care_brochure.pdf> on Jan. 14, 2016, 16 pages.

(Continued)

*Primary Examiner* — Susan T Tran
*Assistant Examiner* — Quanglong N Truong
(74) *Attorney, Agent, or Firm* — Alston & Bird LLP

(57) ABSTRACT

A cosmetic composition is provided. The cosmetic composition includes *Astrocaryum vulgare* oil and/or butter, which is useful in the production and/or protection against degradation of hyaluronic acid in the skin. Also provided are the process for the production of the cosmetic composition and related uses and methods.

9 Claims, 1 Drawing Sheet

(56) References Cited

OTHER PUBLICATIONS

Santos, O. V., et al., "Chemical evaluation and thermal behavior of Brazil nut oil obtained by different extraction processes", Food Research International, Jul. 1, 2012, pp. 253-258, vol. 47, No. 2, Elsevier Ltd.

Thomas, Alfred, et al., "Fats and Fatty Oils", Ullmann's Encyclopedia of Industrial Chemistry, Sep. 30, 2015, 84 pages, Wiley-VCH Verlag GmbH & Co., KGaA, Weinheim.

* cited by examiner

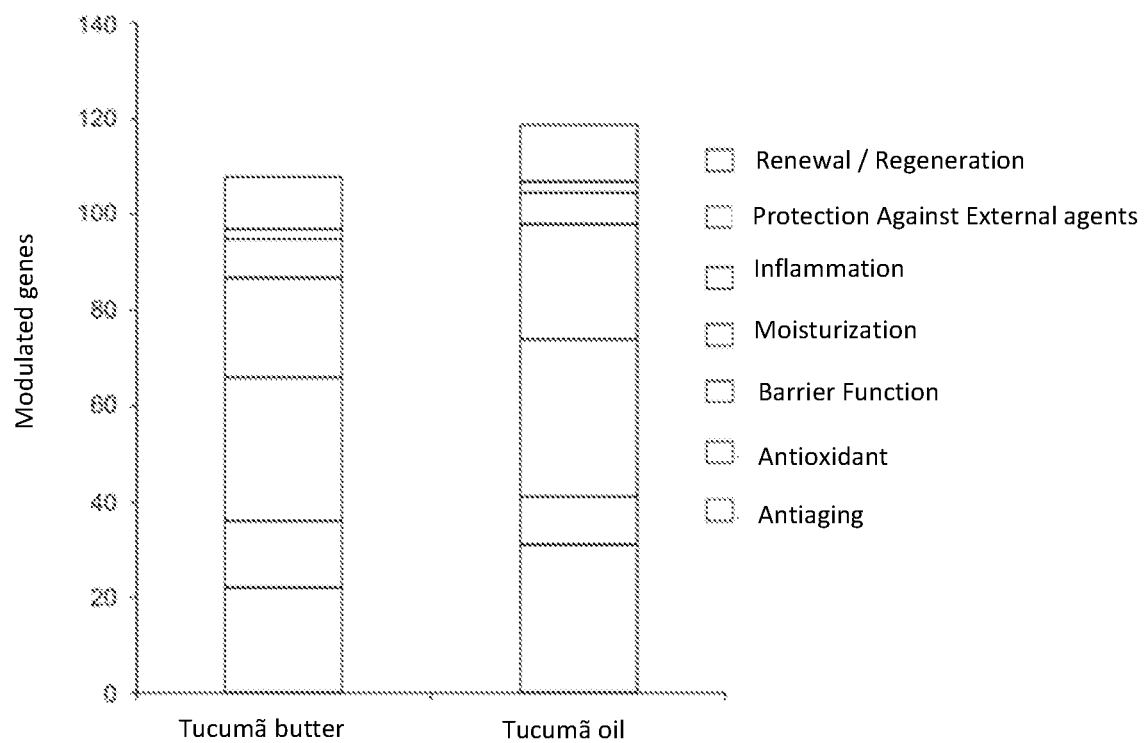
GRAPH – XAMÃ (tucumã) (Fig. 1)

COSMETIC COMPOSITION, METHOD FOR THE PRODUCTION OF *ASTROCARYUM VULGARE* OIL AND/OR BUTTER, USE OF THE COSMETIC COMPOSITION AND METHOD FOR THE PRODUCTION AND/OR PROTECTION AGAINST DEGRADATION OF HYALURONIC ACID IN THE SKIN

CROSS-REFERENCE TO RELATED APPLICATIONS

The present application is a national phase entry of PCT/BR2019/050226, filed on Jun. 17, 2019, which claims the benefit of priority of Brazilian Application No. BR102018072738-9, filed Nov. 5, 2018, the entire contents of which are hereby incorporated by reference in their entirety for all purposes.

TECHNICAL FIELD

The present invention deals with a cosmetic composition comprising *Astrocaryum vulgare* oil and/or butter, which is useful in the endogenous production and/or protection against degradation of hyaluronic acid in the skin, comprising the face and body skin, the process for the production thereof, as well as related uses and methods.

BACKGROUND

Skin aging is the result of several factors that build up over time. In addition to factors intrinsic to each individual, there are external factors such as sun exposure and factors related to style and quality of life, wherein our organism, including the skin, undergoes gradual changes in various physiological processes such as reduced production of essential components for maintaining a healthy skin, as well as acceleration of detrimental processes.

It is known that around the age of thirty, several physiological mechanisms in the skin are compromised and some noticeable clinical signs of skin aging can be perceived, as well as a reduced ability to maintain skin hydration, which can be seen in subsequent years.

From among the mechanisms involved in this process, a decreased production and increased degradation of the hyaluronic acid that is naturally produced in the body is relevant, which affects the face and body skin, causing loss of tissue volume, accentuation of lines and folds, sagging, wrinkles and skin dehydration or dryness.

Endogenous hyaluronic acid comprises a high molecular weight glycosaminoglycan having a negatively charged non-branched linear chain due to the presence of carboxyl groups comprising repetitions of disaccharides glycuronic acid and N-acetylglucosamine. It is a molecule present in the extracellular matrix of many tissues, including the skin. Due to the molecule specific behavior, it has the ability to expand the hydrodynamic volume of the medium in which it is found due to the mutual repulsion of carboxyl groups, hence sequestering water. Thus, due to its ability to retain water in the skin, it acts on deep hydration mechanisms, as well as anti-aging mechanisms such as skin filling.

Endogenous hyaluronic acid is synthesized by specific enzymes designated as SAH (hyaluronic acid synthases) and is catabolized (degraded) by hyaluronidases.

Despite the various treatments currently available, there remains a need for new cosmetic compositions that act on various mechanisms involved in skin aging and skin hydration.

BRIEF SUMMARY

One or more embodiments of the invention may address one or more of the aforementioned problems. Certain embodiments according to the invention provide cosmetic compositions. The cosmetic composition includes *Astrocaryum vulgare* oil and/or butter.

In another aspect, methods of producing *Astrocaryum vulgare* oil and/or butter are provided. The method includes depulping and drying pulp until a moisture of about 7 to about 10% is reached, and cold pressing the dry pulp to obtain the oil. In addition or the alternative, the method includes drying cores until a moisture of about 3 to 8% is reached, breaking the cores, cooking the cores at about 50° C. for about 15 minutes, and cold pressing to obtain the butter.

In yet another aspect, *Astrocaryum vulgare* oil and/or butter is provided. The *Astrocaryum vulgare* oil and/or butter is obtained according to the method described previously herein.

In yet another aspect, methods for the production and/or protection against degradation of hyaluronic acid in the skin are provided. The method includes applying to the skin the cosmetic composition described previously herein.

BRIEF DESCRIPTION OF THE SEVERAL VIEWS OF THE DRAWING(S)

FIG. 1 shows the simultaneous benefits obtained from the oil and butter according to the present invention.

DETAILED DESCRIPTION

The present invention deals with a cosmetic composition characterized by comprising *Astrocaryum vulgare* oil and/or butter.

Although some cosmetic benefits have been suggested to *Astrocaryum vulgare*, also known as "*tucumã*", there is still a need for new compositions that act effectively on the various mechanisms involved in skin aging, particularly in the reduction of production and, simultaneously, in the degradation of hyaluronic acid that is naturally produced by the body.

To this end, a cosmetic composition has now been developed comprising as raw material *Astrocaryum vulgare* oil and/or butter, wherein the oil and/or butter exhibit from about 90 to about 99.9% of the primary metabolite fraction and from about 0.1% to about 10% of secondary metabolites, also designated as bioactive compounds, particularly about 99.5% of the primary metabolite fraction and about 0.5% of secondary metabolites.

It has been surprisingly found that activity on the various mechanisms involved in skin aging, particularly in the reduction of production and, simultaneously, in degradation of the hyaluronic acid naturally generated by the body, is triggered by the combination of primary and secondary metabolites present in *Astrocaryum vulgare* oil and/or butter raw materials.

The primary metabolites according to the present invention comprise, without any limitation, triacylglycerides and the secondary metabolites further comprise, without any limitation, among other compounds, carotenoids, terpenes, glycosides, tannins, flavonoids, phenolic acids, phytosterols (beta-sytosterol at higher concentrations), alpha-tocopherol. The main carotenes being alpha, beta, gamma and delta-carotenes, alpha and beta-cryptoxanthin, neoxanthin and violaxanthin, some of which have not been previously described in *Astrocaryum vulgare*.

According to the present invention, by "raw material" is meant a combination of secondary metabolites with primary metabolites as described herein.

In a particular embodiment, the cosmetic composition according to the present invention comprises the mixture of raw *Astrocaryum vulgare* oil and butter, more particularly containing bioactive compounds or secondary metabolites, in a ratio of about 5:1 to about 1:5, particularly about 2.5:1.

In a preferred embodiment, the present invention contemplates *Astrocaryum vulgare* oil mainly comprising oleic acid (about 65%), palmitic acid (about 25%), stearic acid (about 4%), linolenic acid (about 3%) and linoleic acid (about 2%), wherein its triglyceride composition has high POO (about 35%) and POP (about 14%) levels. *Astrocaryum vulgare* oil contains alpha-tocopherol (about 10 mg/100 g) and phytosterols, beta-sytosterol being present at greater amounts (about 900 mg/kg), and also being rich in carotenoids, about 1200 mg/kg of total carotenoids. The main carotenes identified are: alpha-carotene, beta-carotene, gamma-carotene, delta-carotene, neoxanthin, violaxanthin, alpha-cryptoxanthin and beta-cryptoxanthin.

In a preferred embodiment, the present invention contemplates *Astrocaryum vulgare* butter, which mainly comprises lauric acid (about 50%), myristic acid (about 25%), oleic acid (about 10%), palmitic acid (about 5%), linoleic acid (about 4%), stearic acid (about 2.5%), capric acid (about 2%) and caprylic acid (about 2%), wherein its triglyceride composition has high levels of LaMP (about 30%) and LaMM (about 20%) and has phytosterols in its composition, beta-sytosterol being present at greater amounts (about 980 mg/Kg).

In addition, the cosmetic compositions according to the present invention have anti-aging and antioxidant effects, confer protection against external aggressions, have hydration, anti-inflammatory, integrity/barrier function and skin renewal/regeneration effects. From among the anti-aging effects, stimulation of components of the dermo-epidermis junction are also of importance.

The cosmetic composition according to the present invention can be administered in various cosmetic forms known by the skilled person, for example, body moisturizer, biphasic oil, crude butter, moisturizing body and hand serum.

The cosmetically acceptable excipients according to the present invention are those known to the person skilled in the art for making cosmetic bases in various forms, for example, emulsions, creams, gels, serums, and others known to the person skilled in the art. For example, without any limitation, cosmetically acceptable excipients can be selected from those cited in the "International Cosmetic Ingredient Dictionary & Handbook", 16th Edition. Examples of cosmetically acceptable ingredients are bis-diglyceryl polyacyladipate-1; dodecane; *Prunus amigdalus dulcis* oil; sucrose laurate; xanthan gum, *Helianthus annus* seed oil, glyceryl stearate, cetearyl alcohol, dicaprylyl ether, silica, acrylates/$C_{10-30}$ alkyl acrylate crosspolymer, *Passiflora edulis* seed oil, styrene/acylate copolymer.

In another embodiment, the present invention further contemplates a process for producing *Astrocaryum vulgare* oil and/or butter.

In the production of raw oil and butter, the steps of collection, storage of fruit, seeds and/or pulp of oilseeds are deemed important, as well as the preparation of raw material and extraction of crude oil. In general, when plant oil is intended for edible purposes or for technical purposes where free acidity or color affects the appearance of the end product (cosmetic purposes, for example), the crude oil is refined and the refining steps consist of degumming, neutralization, bleaching and deodorization. However, to ensure benefits to the skin, the refining process must be avoided since removal of secondary metabolites causes loss of the biological activity of these raw materials.

The sequential process of obtaining *Astrocaryum vulgare* oil and butter has been developed to ensure the presence of secondary metabolites (known as bioactive) and to preserve their diversity, as well as the integrity of triacylglycerides. As such, *Astrocaryum vulgare* oil and butter did not undergo any of the known refining steps.

*Astrocaryum vulgare* fruits are collected, dehusked, and can be stored and/or frozen until processing.

Processing is carried out at room temperature and includes the steps of:

depulping on a 8 mm mesh screen with loads of 5 kg/6 minutes at a 60 rpm rotation;

drying the pulp under vacuum until moisture reaches about 7 to about 10%, at a temperature of about 60° C. under vacuum of from about 600 to 720 mmHg. Drying under these conditions is an elementary step to preserve secondary metabolites (considered bioactive according to the present invention) and to prevent them from degrading during processing, which differs from state-of-the-art methods, which employ drying in a rotary dryer or sun exposure;

*Astrocaryum vulgare* cores are dried in recirculating hoods at a temperature of about 50 to about 60° C. for about 7 to about 10 days, until a moisture of about 3 to 8% is reached, under which the almond is found loose inside the core;

cold pressing *Astrocaryum vulgare* dry pulp using an expeller press to obtain *Astrocaryum vulgare* oil, which is filtered and stored for use in the cosmetic compositions according to the present invention;

The dry *Astrocaryum vulgare* core is broken in a roller mill at a rotation of about 50 rpm, after which the almond is separated in a vibrating sieve;

The almond is cooked at 50° C. for about 15 minutes to facilitate pressing of the almond, then it is cold pressed using an expeller press to obtain *tucumã* butter. The butter is filtered and homogenized at about 45° C. and stored for use in the cosmetic compositions according to the present invention.

In another embodiment, the present invention contemplates the use of the cosmetic composition and/or oil and/or butter obtained according to the present invention in stimulating the production and/or protection against degradation of hyaluronic acid in the skin.

This benefit, which is highly desirable in anti-aging compositions having high hydration power, is particularly obtained by using crude oils and butters, combined at a specific ratio, where the butter stimulates the production of hyaluronic acid while the oil protects from degradation (reduced hyaluronidase).

Such a simultaneous and highly desirable effect is particularly provided by the combination according to the present invention, in which a protective effect of reducing hyaluronidase (−38.2%) is observed in the same order of magnitude as the isolated oil (−44%), being complemented by the simultaneous effect of increasing hyaluronic acid (21.5%), which can be comparatively considered a surprising result from the cosmetic point of view.

In another embodiment, the present invention further contemplates a method for producing and/or protecting against degradation of hyaluronic acid in the skin which consists of applying a cosmetic composition according to the present invention to the skin.

The following examples, without any limitation, illustrate the present invention, particularly with regard to obtaining *Astrocaryum vulgare* oil and/or butter according to the present invention, cosmetic compositions and their benefits as described herein.

EXAMPLES

Example 1

Process for Preparing *Astrocaryum vulgare* Oils and/or Butters According to the Present Invention

*Astrocaryum vulgare* fruits were collected, dehusked and stored. The fruits were kept frozen at a temperature of −20° C. until processing. The fruits were thawed at room temperature, around 30° C., and on the second day, after thawing, the fruits were dry depulped, without using any water. The ideal depulping conditions were a 8 mm mesh screen with loads of 5 kg/6 minutes at a 60 rpm rotation. The pulp was subjected to vacuum drying until a moisture of from 8 to 9% was reached at a temperature of 60° C. under a 600 mmHg vacuum.

The cores were then dried in recirculating hoods at a temperature of 55° C. for 8 days, until a moisture of from 5 to 6% is reached, under which the almond is found loose inside the core.

The dried pulp was then cold pressed using an expeller press to obtain the oil. The oil was filtered through a plate frame filter press with the aid of a raw cloth filter element type A. The oil was homogenized and packaged in blue high density polyethylene drums and stored in an inert and fresh environment, preserving the rich diversity of compounds present in the oil.

The dry core was then broken in a roller mill at a rotation of about 50 rpm, after which the almond is separated in a vibrating sieve. The almond was cooked at 50° C. for 15 minutes to facilitate pressing of the almond. The almond was cold pressed using an expeller press to obtain the butter. The butter was filtered through a plate frame filter press with the aid of a raw cloth filter element type A. The butter was homogenized at 45° C. and packaged in blue high density polyethylene drums and stored in an inert and fresh environment, preserving the rich diversity of compounds present in the butter.

The crude oil and butter were chemically characterized by hyphenated techniques, such as gas chromatography, which assessed the triacylglyceride moiety and its fatty acids, as well as phytosterols, gel chromatography, which assessed the glycerol composition, thin layer chromatography which evaluated the phytochemical classes, liquid chromatography coupled to high resolution mass spectrometer Q-Tof, which evaluated the compounds present therein.

Example 2

The Cosmetic Composition According to the Present Invention

TABLE 1

Body moisturizer

| Ingredient | % |
| --- | --- |
| Water | q.s.p. |
| *Astrocarium vulgare* oil | 0.5-2% |
| *Astrocarium vulgare* butter | 2-5% |
| Caprylic/Capric Triglyceride | 2-4% |
| Cetyl Alcohol | 3 |
| Dicaprylyl Carbonate | 2-4% |
| Glycerin | 3 |
| Glyceryl Stearate Citrate | 2 |
| Hydroxyacetophenone | 0.3-0.5% |
| Tocopherol | 0.1-0.3% |
| Polyglyceryl-3 Caprylate | 0.1 |
| Sodium Gluconate | 0.1 |
| Sodium Polyacrylate | 0.4 |
| Tapioca Starch | 1 |
| Propanediol | 2 |

TABLE 2

Body moisturizer

| Ingredient | % |
| --- | --- |
| Water | q.s.p. |
| *Astrocarium vulgare* butter | 2-5% |
| Glycerin | 3 |
| Cetyl Alcohol | 2.94 |
| Glyceryl Stearate Citrate | 2 |
| Caprylic/Capric Triglyceride | 2-4% |
| *Astrocarium vulgare* oil | 0.5-2 |
| Dicaprylyl Carbonate | 1.999-4% |
| Propanediol | 1.998 |
| Tapioca Starch | 1 |
| Hydroxyacetophenone | 0.3-0.5% |
| Sodium Polyacrylate | 0.352 |
| Tocopherol | 0.101-0.3% |
| Sodium Gluconate | 0.1 |
| Polyglyceryl-3 Caprylate | 0.1 |
| Stearyl Alcohol | 0.03 |
| Myristyl Alcohol | 0.03 |

Example 3

Biological Activity

Assessment of oil and/or butter activity according to the present invention was carried out through the gene expression profile and confirmation of protein and/or molecular expression.

FIG. 1 shows the simultaneous benefits obtained from the oil and butter according to the present invention.

The person skilled in the art will be able to readily assess through the teachings of the instant text and examples the advantages of the invention and to propose variations and equivalent alternatives of implementation without departing from the scope of the invention as defined in the appended claims.

The invention claimed is:

1. A cosmetic composition comprising a mixture of crude *Astrocaryum vulgare* oil and butter at a ratio of about 5:1 to about 1:5.

2. The cosmetic composition according to claim 1, wherein the crude oil and butter have from about 90% to about 99.9% of the primary metabolite fraction and from about 0.1% to about 10% of secondary metabolites.

3. The cosmetic composition according to claim 2, wherein the crude oil and butter have about 99.5% of the primary metabolite fraction and about 0.5% of secondary metabolites.

4. The cosmetic composition according to claim 1, wherein the cosmetic composition comprises primary metabolites and secondary metabolites, wherein the primary metabolites comprise tri-acylglycerides and the secondary metabolites comprise carotenoids, terpenes, glycosides, tannins, flavonoids, phenolic acids, phytosterols, alpha-tocopherol, or any combination thereof.

5. The cosmetic composition according to claim 1, wherein the crude *Astrocaryum vulgare* oil comprises about 65% oleic acid, about 25% palmitic acid, about 4% stearic acid, about 3% linolenic acid, and about 2% linoleic acid, wherein the crude *Astrocaryum vulgare* oil has a triglyceride composition of about 35% POO and about 14% POP, about 10 mg/100 g alpha-tocopherol, about 900 mg/Kg beta-sytosterol, and about 1,200 mg/kg carotenoids.

6. The cosmetic composition according to claim 5, wherein the carotenoids comprise alpha-carotene, beta-carotene, gamma-carotene, delta-carotene, neoxanthin, violaxanthin, alpha-cryptoxanthin, and beta-cryptoxanthin.

7. The cosmetic composition according to claim 1, wherein the crude *Astrocaryum vulgare* butter comprises about 50% lauric acid, about 25% myristic acid, about 10% oleic acid, about 5% palmitic acid, about 4% linoleic acid, about 2.5% stearic acid, about 2% capric acid, and about 2% caprylic acid, wherein the crude *Astrocaryum vulgare* butter has a triglyceride composition of about 30% LaMP and about 20% LaMM, and about 980 mg/Kg beta-sytosterol.

8. The cosmetic composition according to claim 1, wherein the cosmetic composition comprises the mixture of crude *Astrocaryum vulgare* oil and butter at a ratio of about 2.5:1.

9. A method for the production and/or protection against degradation of hyaluronic acid in the skin, the method comprising applying to the skin the cosmetic composition according to claim 1.

* * * * *